(12) United States Patent
Meneghini et al.

(10) Patent No.: US 7,828,752 B2
(45) Date of Patent: Nov. 9, 2010

(54) DEVICE AND METHOD FOR LOCATING THE ANTEROPOSTERIOR FEMORAL AXIS TO DETERMINE PROPER FEMORAL COMPONENT ROTATION IN KNEE REPLACEMENT

(75) Inventors: R. Michael Meneghini, Carmel, IN (US); Jeffery L. Pierson, Zionsville, IN (US)

(73) Assignee: Arthroplasty Innovations, LLC, Carmel, IN (US)

( * ) Notice: Subject to any disclaimer, the term of this patent is extended or adjusted under 35 U.S.C. 154(b) by 89 days.

(21) Appl. No.: 11/543,260

(22) Filed: Oct. 5, 2006

(65) Prior Publication Data
US 2008/0139965 A1 Jun. 12, 2008

(51) Int. Cl.
*A61B 5/103* (2006.01)
*A61B 5/117* (2006.01)
*A61B 17/58* (2006.01)
*A61B 17/60* (2006.01)
*A61F 2/00* (2006.01)

(52) U.S. Cl. .......................... 600/587; 606/88; 606/89; 606/96

(58) Field of Classification Search ................. 600/587; 606/88, 89, 96
See application file for complete search history.

(56) References Cited
U.S. PATENT DOCUMENTS

| | | | |
|---|---|---|---|
| 2,416,228 A | * | 2/1947 | Sheppard ..................... 408/105 |
| 2,483,060 A | | 9/1949 | Niedelman et al. |
| 2,592,432 A | | 4/1952 | Kline et al. |
| 4,708,139 A | | 11/1987 | Dunbar, IV |
| 4,739,751 A | | 4/1988 | Sapega et al. |
| 4,781,182 A | | 11/1988 | Purnell et al. |

(Continued)

FOREIGN PATENT DOCUMENTS
EP 0 350 780 1/1990

(Continued)

OTHER PUBLICATIONS

Junichi Arima, MD et al. "Femoral Rotational Alignment, Based on the Anteroposterior Axis, in Total Knee Arthroplasty in a Valgus Knee." *The Journal of Bone and Joint Surgery*. vol. 77-A (1995): 1331-1334.

(Continued)

*Primary Examiner*—Max Hindenburg
*Assistant Examiner*—Sean P Dougherty
(74) *Attorney, Agent, or Firm*—Posz Law Group, PLC (57) ABSTRACT

A device for indicating the location of the anteroposterior femoral axis has a spike or needle that engages the anterior-most point in the intercondylar notch and a rounded or spherical surface is placed on the trochlear groove of the femur and urged in a posterior direction. That is, the rounded surface or ball is urged toward the bottom of the trochlear groove. This causes the rounded surface or ball to self-locate into the deepest point of the trochlear groove. The anterior-most point in the intercondylar notch and the deepest part of the trochlear groove anteriorly are points that accurately determine the anteroposterior femoral axis, and the device includes a marking device or guide member that is fixed perpendicular to this axis. A surgeon, therefore, has an accurate indication of the correct femoral component rotation for proper implant position in a knee replacement or other surgical procedure.

21 Claims, 4 Drawing Sheets

U.S. PATENT DOCUMENTS

| | | | |
|---|---|---|---|
| 4,883,048 | A | 11/1989 | Purnell et al. |
| 4,945,904 | A | 8/1990 | Bolton et al. |
| 5,163,940 | A | 11/1992 | Bourque |
| 5,312,409 | A | 5/1994 | McLaughlin et al. |
| 5,324,296 | A | 6/1994 | Laboureau et al. |
| 5,569,255 | A | 10/1996 | Burke |
| 5,570,706 | A | 11/1996 | Howell |
| 5,624,443 | A * | 4/1997 | Burke ................. 606/86 R |
| 6,019,767 | A | 2/2000 | Howell |
| 6,106,529 | A | 8/2000 | Techiera |
| 6,173,200 | B1 | 1/2001 | Cooke et al. |
| 6,187,011 | B1 | 2/2001 | Torrie |
| 6,254,604 | B1 | 7/2001 | Howell |
| 6,458,135 | B1 | 10/2002 | Harwin et al. |
| 7,060,068 | B2 * | 6/2006 | Tromanhauser et al. ... 606/86 A |
| 2005/0149040 | A1 * | 7/2005 | Haines et al. ............. 606/88 |
| 2005/0209597 | A1 * | 9/2005 | Long et al. ................ 606/86 |
| 2005/0245934 | A1 * | 11/2005 | Tuke et al. ................ 606/79 |
| 2005/0245936 | A1 | 11/2005 | Tuke et al. |
| 2005/0261696 | A1 | 11/2005 | Overes et al. |
| 2006/0195108 | A1 * | 8/2006 | Fox ............................ 606/79 |
| 2006/0195112 | A1 * | 8/2006 | Ek .............................. 606/86 |
| 2007/0016210 | A1 * | 1/2007 | Boehm, Jr. ................ 606/79 |
| 2007/0162038 | A1 * | 7/2007 | Tuke .......................... 606/88 |
| 2008/0306485 | A1 * | 12/2008 | Coon et al. ................ 606/88 |
| 2009/0143784 | A1 * | 6/2009 | Petersen et al. ........... 606/96 |

FOREIGN PATENT DOCUMENTS

| | | |
|---|---|---|
| FR | 2716364 | 8/1995 |
| GB | 2 322 304 | 8/1998 |
| WO | WO 95/19141 | 7/1995 |

OTHER PUBLICATIONS

Leo A. Whiteside, MD et al. "The Anteroposterior Axis for Femoral Rotational Alignment in a in a Valgus Knee Arthroplasty." *Clinical Orthopedics and Related Research* vol. 321 (1995): 168-172.

Bernd Stoeckl, MD et al. "Reliability of the Transepicondylar Axis as an Anatomical Landmark in Total Knee Arthroplasty." *The Journal of Arthroplasty*. vol. 21 No. 6 (2006): 878-882.

S.H. Palmer et al. "A New Technique for the Assessment of Intra-operative Femoral Component Rotation in Total Knee Arthroplasty: The Anterior Femoral Cortical Line." Publication date: unknown. 1-7.

Richard Scott, MD "Trans-sulcus Angle Guide." *Innomed Orthopedic Instruments*. Publication date: unknown.

* cited by examiner

DEVICE AND METHOD FOR LOCATING THE ANTEROPOSTERIOR FEMORAL AXIS TO DETERMINE PROPER FEMORAL COMPONENT ROTATION IN KNEE REPLACEMENT

BACKGROUND OF THE INVENTION

The present invention relates to a device for establishing proper femoral component rotation in, for example, knee replacement surgery, and more particularly to a device for locating the anteroposterior femoral axis and for locating a line parallel or substantially parallel to the transepicondylar axis of a human femur based on the location of the anteroposterior femoral axis.

Establishing proper femoral component rotation is critical to the success of knee replacement surgery. There are a variety of anatomic landmarks that are used intraoperatively by the surgeon to ascertain the proper rotation and include the posterior femoral condyles, the transepicondylar axis and the anteroposterior femoral axis, or Whiteside's line.

The posterior condylar axis is frequently used as the reference for femoral component rotation; however, this landmark may be less accurate due to erosion from the arthritic process, particularly in the valgus knee.

The transepicondylar axis has been shown to be a reliable reference for placement of the femoral component in correct rotation; however, accurately determining the correct medial and lateral femoral epicondyles requires additional soft-tissue dissection. Also, the accuracy and reproducibility of defining the transepicondylar axis have been difficult to establish. See Stoeckl, Nogler, Krismer, Beimel, de la Barrera, & Kessler, *Reliability of the Transepicondylar Axis as an Anatomical Landmark in Total Knee Arthroplasty*, The Journal of Arthroplasty Vol. 21 No. 6 (2006).

The anteroposterior femoral axis of the femoral groove has been shown to be an accurate reference point for determining the correct femoral component rotation. A line perpendicular to the anteroposterior femoral axis has been shown to accurately indicate the transepicondylar axis and is even more accurate than the epicondylar axis in valgus knees for determining the correct femoral component rotation. For this reason, many surgeons use the anteroposterior femoral axis reference as the landmark of choice for determining femoral component rotation in total knee replacement surgery.

The anteroposterior femoral axis, or Whiteside's line, can be determined by the lowest point of the trochlear groove, or trochlear sulcus, and the anteroposterior point of the intercondylar notch. In other words, the anteroposterior femoral axis is a line drawn from the deepest part of the trochlear groove anteriorly to the center of the intercondylar notch posteriorly. The anteroposterior femoral axis, or Whiteside's line, can also be defined as a line through the deepest part of the patellar groove anteriorly and the center of the intercondylar notch posteriorly.

With emerging and popular minimally invasive surgical techniques in total knee replacement, the soft-tissue dissection required to accurately determine the transepicondylar axis is not practical. This requires the surgeon to rely solely on an accurate determination of the anteroposterior femoral axis to enact proper femoral component rotation. This axis is typically "eyeballed" by the operating surgeon with the use of marks made with an electrocautery device or a marking pen and then determining a perpendicular line to that free-hand. This method is inherently inaccurate, which prompted the present inventors to create a device and method that accurately, reproducibly and efficiently locates the anteroposterior femoral axis.

SUMMARY OF THE INVENTION

A device for approximating the location of the anteroposterior femoral axis includes a body; an upper engagement member that is connected to the body; and a lower engagement member that is connected to the body. The lower engagement member and the upper engagement member are spaced apart, and when the lower engagement member engages a predetermined location in the intercondylar notch of the femur and the upper engagement member engages the trochlear groove of the femur, a line extending between the upper engagement member and the lower engagement member approximates the location of the anteroposterior femoral axis.

In another aspect of the invention, the lower engagement member is a spike or a needle, which has a point for engaging the intercondylar notch.

In another aspect of the invention, the upper engagement member includes a rounded surface for settling in substantially the deepest part of the trochlear groove when urged in a downward direction while engaging the trochlear groove.

In another aspect of the invention, the predetermined location in the intercondylar notch is the anterior-most point of the intercondylar notch.

In another aspect of the invention, the device includes a guide member connected to the body. The guide member indicates a line that is perpendicular to the anteroposterior femoral axis and substantially parallel to the transepicondylar axis.

In another aspect of the invention, the guide member includes a drill guide for guiding a drill.

In another aspect of the invention, the rounded surface is substantially spherical and is sized such that it will settle into the bottom of the trochlear groove.

In another aspect of the invention, the upper engagement member is attached to an upper arm that extends from the body, and the upper arm is coupled to the body to move with respect to the body such that the distance between the upper engagement member and the lower engagement member can be varied to accommodate femurs of different sizes.

In another aspect of the invention, the drill guide is fixed with respect to the upper arm such that the drill guide moves together with the upper arm when the upper arm moves with respect to the body.

The invention includes a method of indicating the location of the anteroposterior femoral axis. The method includes: manually positioning a lower engagement member of a hand held device in the intercondylar notch of the femur such that the lower engagement member is engaged with a predetermined point of the intercondylar notch of the femur; manually positioning an upper engagement member in the trochlear groove of the femur while urging the upper engagement member into the bottom of the trochlear groove; and using a guide member, which is part of the device and is fixed with respect to the upper and lower engagement members, to indicate the location of a guide line, which is substantially parallel to the transepicondylar axis.

BRIEF DESCRIPTION OF THE DRAWINGS

The accompanying figures, in which like reference numerals refer to identical or functionally similar elements throughout the separate views and which, together with the detailed description below, are incorporated in and form part of the specification, serve to further illustrate various embodiments and to explain various principles and advantages all in accordance with the present invention.

DETAILED DESCRIPTION OF THE PREFERRED EMBODIMENTS

Figure 1:
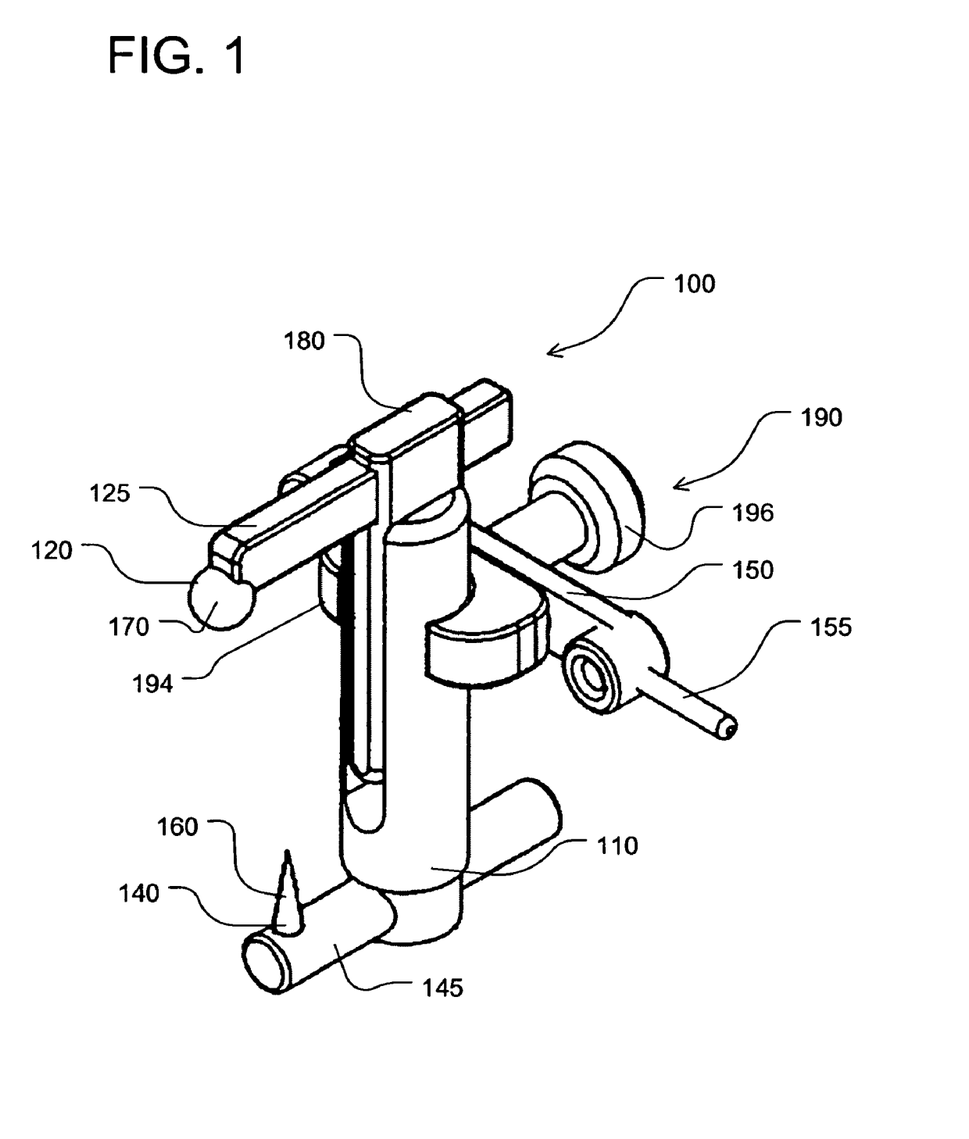
FIG. 1 is a perspective view of a device for approximating the location of the anteroposterior femoral axis.
Figure 2:
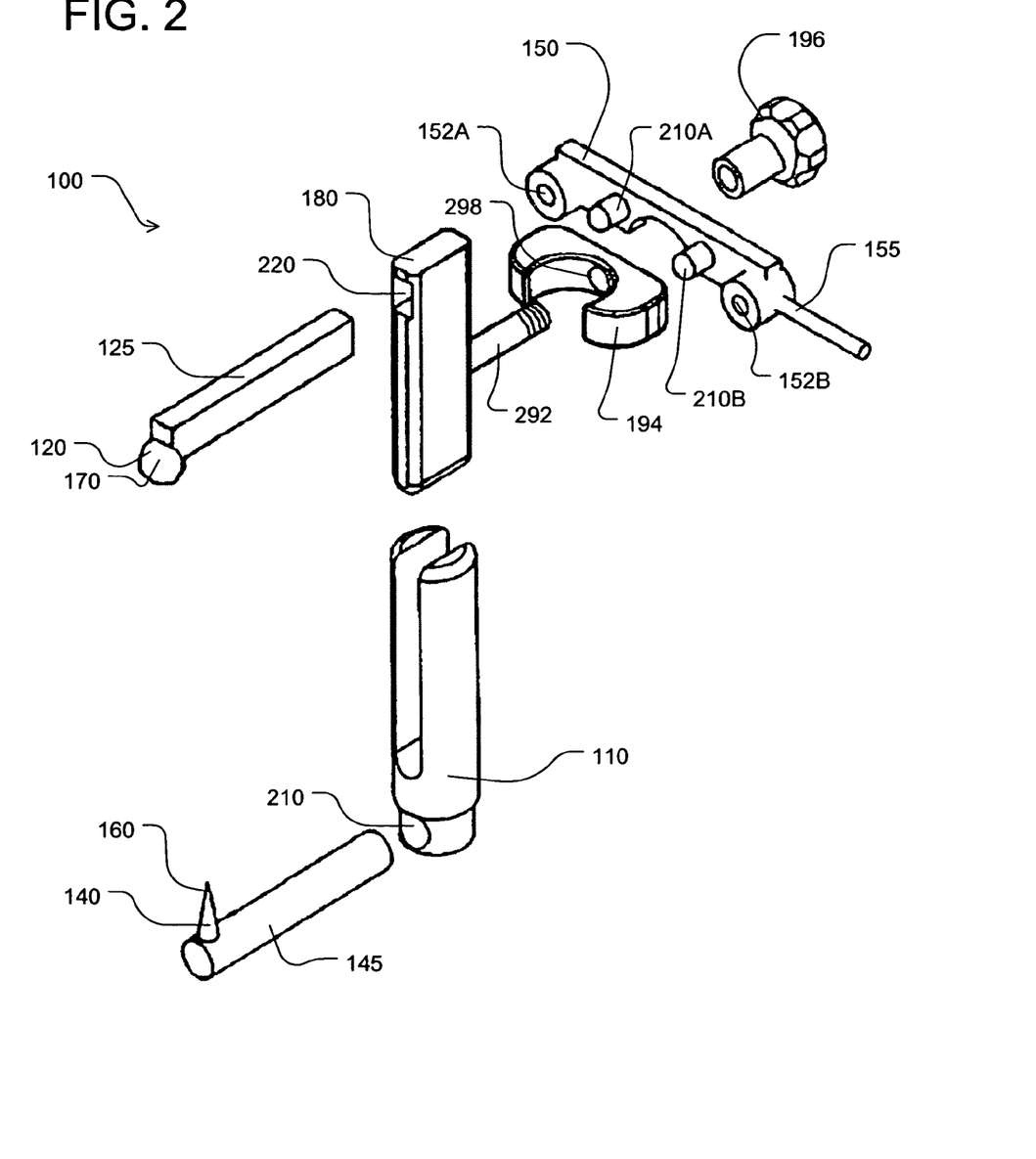
FIG. 2 is an exploded view of the device of FIG. 1.
Figure 3:
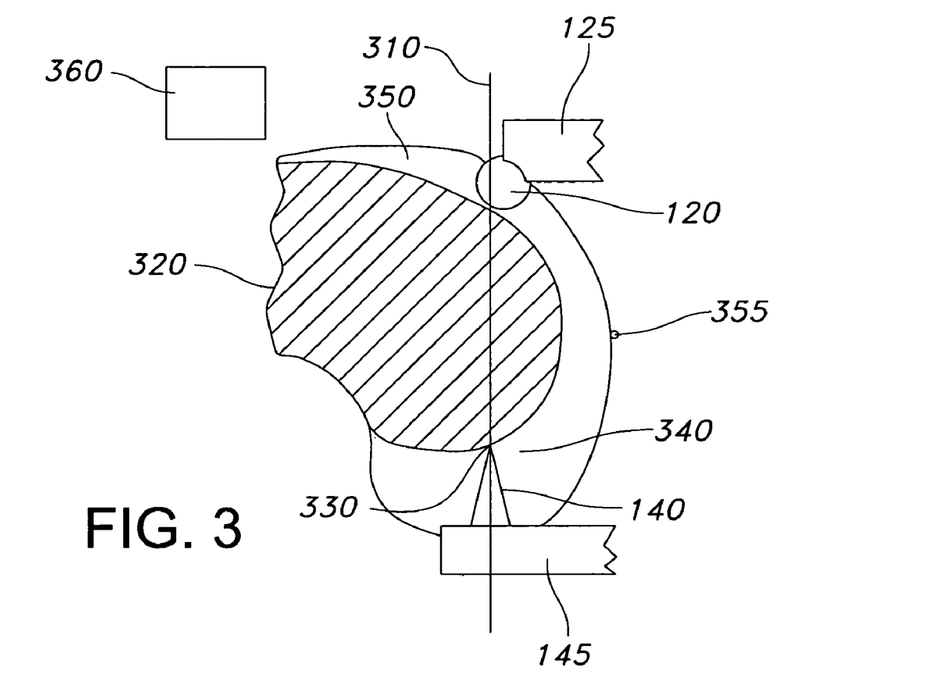
FIG. 3 is a partial diagrammatic cross sectional view of a femur, which is horizontal, while the device of FIG. 1 engages the femur.
Figure 4:
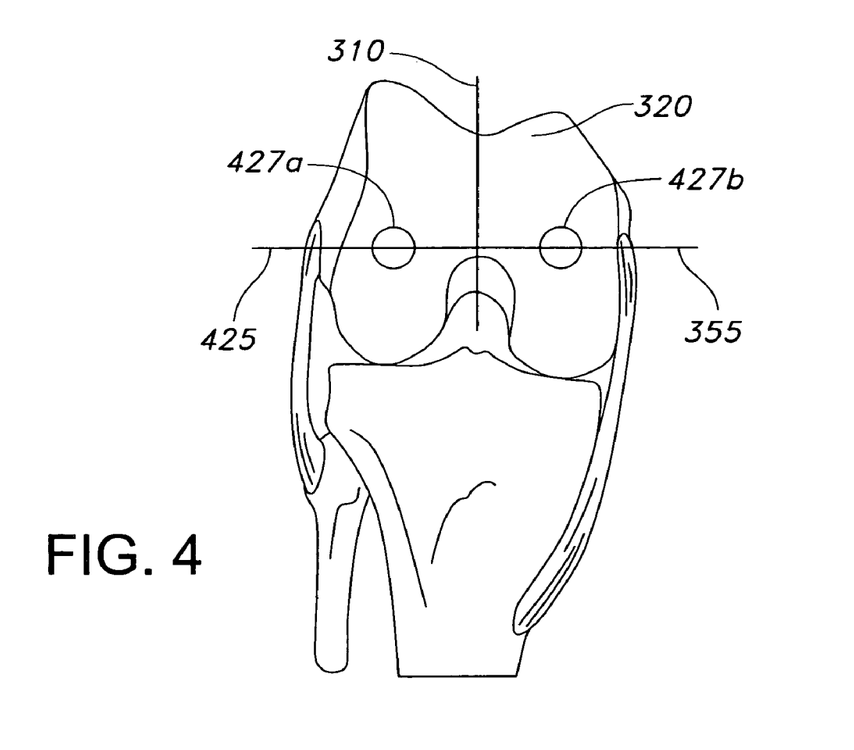
FIG. 4 is a diagrammatic front view of a knee when the femur is substantially horizontal and the tibia is substantially vertical.

FIGS. 1 and 2 show a device 100 for approximating the location of the anteroposterior femoral axis 310 (See FIGS. 3 and 4). The device 100 includes a body 110. An upper engagement member 120 is connected to the body by an upper arm 125, and a lower engagement member 140 is connected to the body 110 by a lower arm 145. The lower engagement member 140 and the upper engagement member 120 are spaced apart, as shown.

As shown in FIG. 3, when the lower engagement member 140 engages a predetermined location 330 in the intercondylar notch 340 of the femur 320 and the upper engagement member 120 engages the trochlear groove 350 of the femur 320, a line extending between the upper engagement member 120 and the lower engagement member 140 approximates the location of the anteroposterior femoral axis 310, which, as explained above, is a valuable reference line for determining proper femoral rotation in knee replacement surgery.

As shown in FIGS. 1 and 2, the lower engagement member 140 is preferably a spike or a needle 160, which has a pointed tip for engaging the predetermined location 330 in the intercondylar notch 340. The spike or needle 160 is fixed rigidly to the lower arm 145 and extends generally toward the upper engagement member 120. In the embodiment of FIGS. 1-3, the lower engagement member 140 is formed by a conical spike 160, as shown.

The predetermined location 330 is preferably the anterior-most point of the intercondylar notch 340. The surgeon finds the anterior-most point of the intercondylar notch 340 and embeds the tip of the lower engagement member 140 at this point 330. Assuming the patient is positioned such that the longitudinal axis of the femur 320 is horizontal and the intercondylar notch 340 is generally facing downward, as shown in FIG. 3, the spike or needle 160 is urged in an upward direction into the anterior-most point 330 of the intercondylar notch 340 in the first step of using the device 100. That is, the spike or needle 160 penetrates the femur 320 such that the lower engagement member 140 is fixed and serves as a pivot point for the remainder of the device 100 when the device 100 is being manipulated.

In practice, the patient is not normally positioned so that the femur 320 is in a horizontal position during knee replacement surgery. However, FIG. 3 is used to give a frame of reference for terms such as "upward" and "downward" herein.

The lower arm 145 can be coupled to the body 110 in an adjustable fashion such that the distance between the lower engagement member 140 and the body 110 can be varied to accommodate femurs of various sizes and femurs in which a distal cut has been made, which alters the dimensions of the femur 320. In particular, an opening 210 is formed in the lower end of the body 110 for receiving the lower arm 145. Although not illustrated, a holding mechanism, which can be a known set screw or friction coupling, for example, is employed to secure the lower arm 145 to the body 110. The holding mechanism permits the lower arm 145 to slide with respect to the body 110 in the direction of the longitudinal axis of the lower arm 145 when adjustment is desired. Otherwise, the holding mechanism firmly holds the lower arm 145 in position when the device 100 is being used to locate the anteroposterior femoral axis 310.

The upper engagement member 120 includes a rounded surface 170 or is otherwise shaped for settling in the deepest part of the trochlear groove 350 when urged in a downward direction, or toward the lower engagement member 140. The rounded surface 170 is shaped to self-locate the bottom of the trochlear groove 350 when urged toward the lower engagement member 140. The rounded surface 170 is preferably a spherical surface formed at or near the distal end of the upper arm 125. The rounded surface 170 is sized such that it will settle into the bottom, or the deepest part, of the trochlear groove 350. In other words, the rounded surface 170 finds the deepest part of the patellar groove anteriorly when guided by a surgeon. For example, in a prototype of the invention, a preferred diameter of a sphere forming the rounded surface 170 is 0.250 inches.

The upper arm 125 can be coupled to the body 110 in an adjustable fashion such that the distance between the upper engagement member 120 and the body 110 can be varied. In particular, an opening 220 is formed in the upper end of an inner support member 180, which is coupled to the body 110, for receiving the upper arm 125. Although not illustrated, a holding mechanism, which can be a known set screw or friction coupling, for example, is employed to secure the upper arm 125 to the inner support member 180. The holding mechanism permits the upper arm 125 to slide with respect to the inner support member 180 in the direction of the longitudinal axis of the upper arm 125 when adjustment is desired. The holding mechanism firmly holds the upper arm 125 in position when the device 100 is being used to locate the anteroposterior femoral axis 310 but permits adjustment when desired.

In addition, the upper arm 125 is coupled to the body 110 to move with respect to the body 110 such that the distance between the upper engagement member 120 and the lower engagement member 140 can be varied to accommodate femurs of different sizes. In particular, the inner support member 180 slides with respect to the body 110 in the direction of the longitudinal axis of the body 110 to permit the distance between the upper engagement member 120 and the lower engagement member 140 to be varied. A locking mechanism 190 locks the inner support member 180 to the body 110 when the device 100 is being used.

The locking mechanism 190 includes a stud 292, a saddle 194, and a nut 196. An opening 298 in the saddle receives the stud 292, as shown in the exploded view of FIG. 2. A distal end of the stud 292 is threaded. When the device 100 is assembled as shown in FIG. 1, the stud passes through the saddle 194 and is threaded into the nut 196. The saddle 194 wraps around the body 110 and clamps the body 110 onto the inner support member 180 when the nut 196 is tightened. When the nut 196 is loosened, the saddle 194 releases the inner support member 180 and permits the inner support member 180 to slide with respect to the body 110. When the nut 196 is tightened, the inner support member 180 is fixed to the body 110.

The device 100 includes a guide member 150, which is connected to the body 110 such that the guide member 150 is perpendicular to a line extending between the center of the upper engagement member 120 and the center of the lower engagement member 140. The guide member 150 indicates a guide line 355 that is perpendicular to the anteroposterior femoral axis 310 and substantially parallel to the transepicondylar axis 425. The guide member 150 indicates the guide line 355 as the line extending between a pair of drill guide holes 152A, 152B which are formed in the guide member 150 and are spaced apart as shown. In other words, the centers of the holes 152A, 152B define the guide line 355.

The holes 152A, 152B are located such that a line extending between their centers is perpendicular to a line extending between the tip of the lower engagement member 140 and a center of the upper engagement member 120. In other words, when the device 100 is properly positioned during surgery, a line extending between the centers of the holes 152A, 152B should be substantially perpendicular to the anteroposterior femoral axis 310. Since the transepicondylar axis 425 is substantially perpendicular to the anteroposterior femoral axis 310, the guide line 355 is substantially parallel to the transepicondylar axis 425. Thus, the guide member 150 indicates the location of a line (the guide line 355) that is parallel or substantially parallel to the transepicondylar axis 425 of a femur 320. The guide line 355 can be used to indicate femoral rotation in knee replacement surgery.

The surgeon can use the holes 152A, 152B as drill guides to guide a drill (not illustrated) to form holes 427A, 427B in the femur 320. The holes 427A, 427B will be located on the guide line 355. That is, a line extending between the centers of the holes 427A, 427B will be substantially parallel to the transepicondylar axis 425 and substantially perpendicular to the anteroposterior femoral axis 310.

Although the illustrated embodiment shows drill guide holes 152A, 152B formed in the guide member 150, the guide member 150 can be a straight edge to serve as a guide for drawing the guide line 355 with ink or as a guide for some other known marking method.

The guide member 150 can include an extension 155, which lies approximately on the guide line 355 and provides the surgeon with a visual representation of the guide line 355.

In the preferred and illustrated embodiment, the guide member 150 is fixed with respect to the upper arm 125 such that the guide member 150 moves together with the upper arm 125 when the upper arm 125 moves with respect to the body 110 during adjustment.

The guide member 150 is coupled to the saddle 194. In the preferred and illustrated embodiment, a pair of protrusions 210A, 210B extends from the guide member 150 toward the saddle 194. The protrusions 210A, 210B are received by openings (not illustrated) in the saddle 194 to hold the guide member 150 into position. The guide member 150 is clamped between the nut 196 and the saddle 194 when the nut 196 is tightened.

Thus, a method of indicating the location of the anteroposterior femoral axis 310 includes manually positioning the lower engagement member 140 of the hand held device 100 in the intercondylar notch 330 of the femur 320 such that the lower engagement member 140 is engaged with the predetermined point 330 of the intercondylar notch 330 of the femur 320. The predetermined point 330 is the anteroposterior point of the intercondylar notch. Next, the upper engagement member 120 is engaged in the trochlear groove 350 while urging the upper engagement member 120 into the bottom of the trochlear groove 350 to find the deepest part of the trochlear groove 350 anteriorly. Then, the guide member 150, which is part of the device and is fixed with respect to the upper and lower engagement members, is used to indicate the location of a guide line, which is parallel or substantially parallel to the transepicondylar axis 425.

While the lower engagement member 140 is engaged with the femur 320, the upper engagement member 120 can move within the trochlear groove 350, since the upper engagement member 120 includes a rounded surface 170 and the device 100 can pivot about the point where the lower engagement member 140 engages with the femur 320. During such movement, the line extending between the tip of the lower engagement member 140 and the center of the upper engagement member 120 will move within a generally vertical plane 360. The anteroposterior femoral axis 310 lies substantially within the vertical plane 360. Thus, even if the line extending between the tip of the lower engagement member 140 and the center of the upper engagement member 120 does not coincide with the anteroposterior femoral axis 310, the guide line 355 determined by the guide member 150 will be substantially perpendicular to the vertical plane 360 and thus will be substantially perpendicular to the anteroposterior femoral axis 310. Therefore, the guide line 355 will be useful and will be parallel or substantially parallel to the transepicondylar axis 425 even if the device does not accurately locate the anteroposterior femoral axis 310, as long as the line extending between the tip of the lower engagement member 140 and the center of the upper engagement member 120 is substantially within the same plane as the anteroposterior femoral axis 310.

The vertical plane 360 is not truly vertical, but rather in slight valgus (more so in females). So in truth, as the upper engagement member 120 moves proximally, the anteroposterior femoral axis 310 will theoretically be positioned into more external rotation. However, speaking generally and approximately, the plane 360 is referred to as "vertical."

The unique principle that enables the correct determination of the anteroposterior femoral axis 310, which indicates the location of the guide line 355, which is parallel or substantially parallel to the transepicondylar axis 425 due to the substantially perpendicular relationship between the anteroposterior femoral axis 310 and the transepicondylar axis 425, is the accurate determination of the two distinct points that create the anteroposterior femoral axis 310: the anterior-most point of the intercondylar notch 330 and a point a the bottom or the deepest part of the trochlear groove 350. This device requires the surgeon to determine the anterior-most point in the intercondylar notch, which may require removal of encroaching notch osteophytes; however, the device automatically and reproducibly determines the deepest portion of the trochlear groove 350.

The posterior-most point in the trochlear groove 350 is determined based on the principle that a rounded object of a given radius of curvature will find the lowest point of a concavity if a downward force is placed on the rounded object toward the concave shape.

The device 100 has a spike or point 160 that engages the anterior-most point in the intercondylar notch, and a rounded surface or ball 170 is placed on the trochlear groove 350 of the femur 320 and urged in a posterior direction. That is, the rounded surface or ball 170 is urged toward the bottom of the trochlear groove 350. This causes the rounded surface or ball 170 to self-locate into a point at the deepest part of the trochlear groove 350. These two points accurately determine the anteroposterior femoral axis 310.

The device includes a marking device or guide member 150 that is fixed perpendicular to the line extending between the tip of the lower engagement member 140 and the center of the upper engagement member 120, which approximately coincides with the anteroposterior femoral axis 310. Thus, when the device is properly positioned on the femur 320, the surgeon has an accurate indication of the correct femoral component rotation for proper implant position in a knee replacement procedure.

Figure 5:
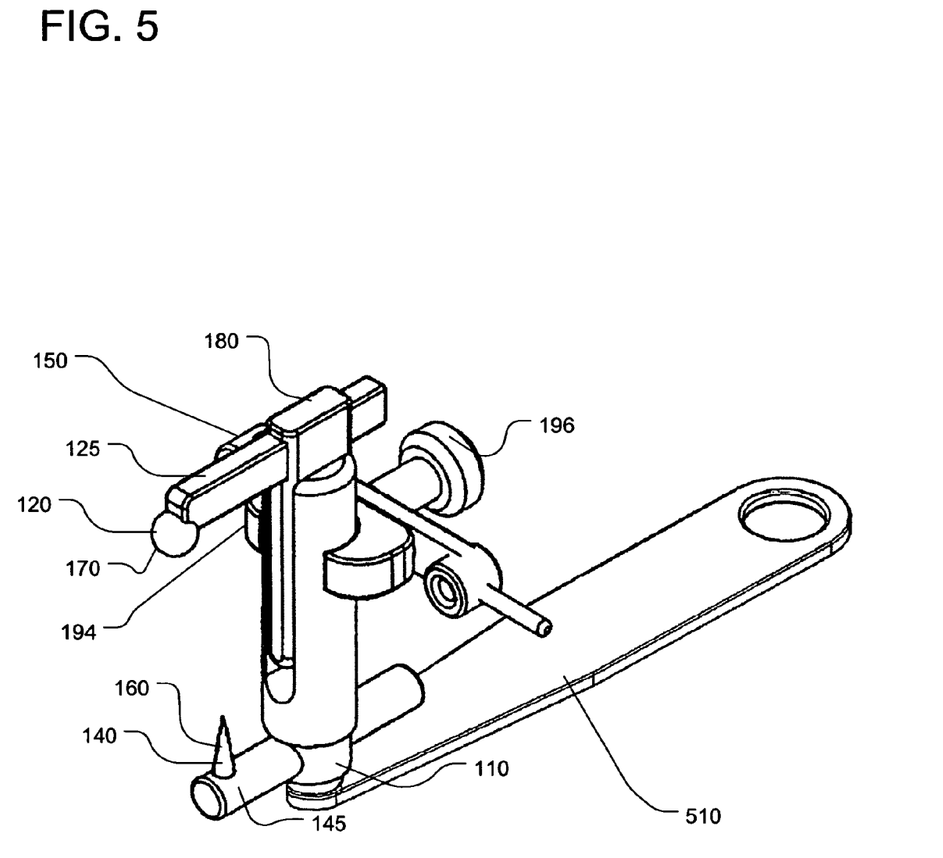
FIG. 5 is a perspective view of a further embodiment of a device for approximating the location of the anteroposterior femoral axis.

FIG. 5 illustrates a further embodiment of the device in which a handle 510 is fixed to the lower end of the body 110. The handle 510 helps a surgeon to stabilize the device 100.

In another embodiment (not illustrated), the upper arm can simply be a cylindrical rod that extends from the body 110 in the same manner as the illustrated upper arm 125, and the distal end of the cylindrical rod can serve as the upper engagement member. Since the cylindrical rod has a rounded surface, the lower surface of the cylindrical rod can serve as the upper engagement member as long as the cylindrical rod is sized to self-locate in the lowest or deepest part of the trochlear groove 350. Other shapes that tend to self-locate themselves into the lowest or deepest part of the trochlear groove 350 can also be employed as the upper engagement member.

In another embodiment (not illustrated) a bearing is located between the lower arm 145 and the body 110 so that the lower arm 145 rotates about its longitudinal axis. This motion permits the body to pivot with respect to the lower arm 145 when fitting the upper engagement member 120 into the trochlear groove 350.

This disclosure is intended to explain how to fashion and use various embodiments in accordance with the invention rather than to limit the true, intended, and fair scope and spirit thereof. The foregoing description is not intended to be exhaustive or to limit the invention to the precise form disclosed. Modifications or variations are possible in light of the above teachings. The embodiments were chosen and described to provide the best illustration of the principles of the invention and its practical application, and to enable one of ordinary skill in the art to utilize the invention in various embodiments and with various modifications as are suited to the particular use contemplated. All such modifications and variations are within the scope of the invention as determined by the appended claims, as may be amended during the pendency of this application for patent, and all equivalents thereof, when interpreted in accordance with the breadth to which they are fairly, legally, and equitably entitled.

The invention claimed is:

1. A device for approximating a location of an anteroposterior femoral axis, or Whiteside's line, wherein the anteroposterior femoral axis is located at a lower end of a human femur, the device comprising:
    a body;
    an upper arm, which extends from the body;
    an upper engagement member that projects from the upper arm;
    a lower arm, which extends from the body,
    a lower engagement member that projects from a distal end of the lower arm, wherein
    the lower engagement member and the upper engagement member are spaced apart,
    a distal end of the lower engagement member is adapted to engage an anterior-most point within an intercondylar notch of the femur, when an axis of the lower arm lies generally in an anteroposterior plane, in which the femoral axis also lies,
    the upper engagement member is adapted to settle substantially in a deepest part of a trochlear groove of the femur, when the upper engagement member is urged toward the lower engagement member and when an axis of the upper arm lies generally in the anteroposterior plane, wherein
    the device is constructed and arranged so that when the lower engagement member engages the anterior-most point within the intercondylar notch of the femur and the upper engagement member engages substantially the deepest part of the trochlear groove of the femur, a line extending between the upper engagement member and the lower engagement member approximates the location of Whiteside's line.

2. The device of claim 1, wherein the lower engagement member is a spike or a needle, which is conical and has a single point for engaging the anterior-most point within the intercondylar notch.

3. The device of claim 1, wherein the device includes a guide member connected to the body, wherein the guide member has a longitudinal dimension that extends perpendicularly to the axes of the upper and lower arms and indicates a guide line that is perpendicular to and spaced apart from the line extending between the upper engagement member and the lower engagement member.

4. The device according to claim 3, wherein the guide member includes a drill guide for guiding a drill, and the drill guide includes a drill guide hole, and an axis of the drill guide hole extends in a direction that is perpendicular to and spaced apart from the line extending between the upper engagement member and the lower engagement member.

5. The device according to claim 1, wherein the upper engagement member and the lower engagement member are constructed and arranged so that the line extending between the upper engagement member and the lower engagement member approximates the location of Whiteside's line when the lower engagement member engages the anterior-most point of the intercondylar notch.

6. The device according to claim 1, wherein the upper engagement member is substantially spherical and is sized such that the upper engagement member will settle into the deepest part of the trochlear groove when the upper arm extends parallel to the femoral axis.

7. The device according to claim 1, wherein the upper arm is coupled to the body to move with respect to the body such that the distance between the upper engagement member and the lower engagement member can be varied to accommodate femurs of different sizes.

8. The device according to claim 7, wherein the device includes a drill guide, and the drill guide is fixed with respect to the upper arm such that the drill guide moves together with the upper arm when the upper arm moves with respect to the body.

9. The device according to claim 3, wherein the guide member includes a drill guide for indicating a location where a hole is to be formed in the femur, and the drill guide includes a drill guide hole, and an axis of the drill guide hole extends in a direction that is perpendicular to and spaced apart from the line extending between the upper engagement member and the lower engagement member.

10. A device for indicating a location of a guide line that is substantially parallel to a transepicondylar axis, wherein the transepicondylar axis is located at the lower end of a human femur, the device comprising:
    a body;
    a first arm that extends from the body, wherein the first arm includes a rounded surface;
    a second arm that extends from the body, wherein a spike projects from the second arm, wherein the spike and the rounded surface are spaced apart and the spike extends toward the rounded surface; and a guide member that is fixed to the body, wherein the guide member has a longitudinal dimension that extends perpendicularly to a line extending directly between the spike and the rounded surface, the rounded surface is adapted to engage a bottom of a trochlear groove of the femur when the guide member is perpendicular to a femoral axis and when an axis of the first arm lies in an anteroposterior plane, in which the femoral axis also lies, a distal end of the spike is pointed, and the pointed distal end of the spike is adapted to engage an anterior-most point within an intercondylar notch of a femur when the guide member is perpendicular to the femoral axis and when an axis of the second arm lies in the anteroposterior plane, wherein the device is in a fully engaged position when a distal end of the spike is fixed to the anterior-most point within the intercondylar notch of the femur, the guide member is perpendicular to the femoral axis, and, simultaneously, the rounded surface is settled at the bottom of the trochlear groove of the femur, and the guide line that is indicated by the guide member when the device is in the fully engaged position is perpendicular to and spaced apart from a line extending between the spike and the rounded surface and substantially parallel to the transepicondylar axis.

11. The device according to claim 10, wherein the device is constructed and arranged so that the line extending between the spike and the rounded surface approximates an anteroposterior axis of the lower end of the femur, or Whiteside's line, when the distal end of the spike is fixed at the anterior-most point within the intercondylar notch of the femur and the rounded surface is settled at the bottom of the trochlear groove of the femur.

12. The device according to claim 10, wherein the rounded surface is spherical and is sized such that the rounded surface will contact a lowest point of the trochlear groove.

13. The device according to claim 10, wherein the rounded surface and the spike are constructed and adapted to lie in the anteroposterior plane when the distal end of the spike is fixed at the anterior-most point within the intercondylar notch and when the rounded surface contacts the bottom of the trochlear groove of the femur.

14. The device according to claim 11, wherein the guide member includes a drill guide hole for guiding a drill, and an axis of the drill guide hole is perpendicular to and spaced apart from the line that extends between the spike and the rounded surface.

15. The device according to claim 1, wherein the lower engagement member is a conical member.

16. The device according to claim 15, wherein a longitudinal axis of the conical member lies in a plane that generally passes through a center of the upper engagement member.

17. The device according to claim 1, wherein the lower engagement member is generally longitudinal, and a longitudinal axis of the lower engagement member lies in the anteroposterior plane, which passes generally through a center of the upper engagement member.

18. The device according to claim 1, wherein the device includes a drill guide, which includes a pair of drill guide holes that are spaced apart from one another, and axes of the drill guide holes are located on opposite sides of, are perpendicular to, and are spaced apart from the line extending between the upper engagement member and the lower engagement member.

19. The device according to claim 4, wherein the drill guide hole is one of a pair of drill guide holes, the axes of which are parallel.

20. A device for indicating locations of two holes to be drilled in a lower end of a human femur in a knee replacement, the device comprising:

a body;

a first arm that extends from the body, wherein the first arm includes a rounded surface;

a second arm that extends from the body, wherein a spike projects from the second arm, wherein the spike and the rounded surface are spaced apart and the spike extends toward the rounded surface; and a guide member that is attached to the body, wherein the guide member has a longitudinal dimension that extends perpendicularly to a line extending directly between the spike and the rounded surface, the rounded surface is adapted to engage a bottom of a trochlear groove of the femur when the guide member is perpendicular to a femoral axis and when an axis of the first arm lies in an anteroposterior plane, in which the femoral axis also lies, the spike has a pointed distal end, and the pointed distal end of the spike is adapted to engage an anterior-most point within an intercondylar notch of a femur when the guide member is perpendicular to the femoral axis and when an axis of the second arm lies in the anteroposterior plane, the guide member includes a pair of drill guide openings for guiding a drill, wherein axes of the drill guide openings are parallel to one another, the drill guide openings indicate locations of the holes to be drilled in the lower end of a human femur when the device is in a fully engaged position, the device is in the fully engaged position when a distal end of the spike is fixed to the anterior-most point within the intercondylar notch of the femur, the guide member is perpendicular to the femoral axis, and simultaneously, the rounded surface is settled at the bottom of the trochlear groove of the femur, and the drill guide openings are spaced apart from one another in a lateral direction of the drill guide, so that a first one of the holes is located on a first side of a central plane that passes through the body and the spike and the rounded surface, and a second one of the holes is located on a second side of the central plane, wherein the first side of the central plane is opposite to the second side of the central plane.

21. The device of claim 20, wherein the guide member is constructed to slide in a longitudinal direction of the body so that a position of the guide member with respect to the body can be adjusted in a direction that is generally parallel to the line extending between the spike and the rounded surface; and the device includes a locking mechanism for locking and unlocking the guide member with respect to the body.

* * * * *